United States Patent
Jensen et al.

(10) Patent No.: US 9,451,992 B2
(45) Date of Patent: Sep. 27, 2016

(54) VARIABLE ANGLE BONE SCREW FIXATION ARRANGEMENT

(75) Inventors: Harm-Iven Jensen, Noer (DE); Helmut D. Link, Hamburg (DE)

(73) Assignee: Facet-Link Inc., Rockaway, NJ (US)

( * ) Notice: Subject to any disclaimer, the term of this patent is extended or adjusted under 35 U.S.C. 154(b) by 5 days.

(21) Appl. No.: 13/309,245

(22) Filed: Dec. 1, 2011

(65) Prior Publication Data

US 2012/0143262 A1 Jun. 7, 2012

Related U.S. Application Data

(60) Provisional application No. 61/418,662, filed on Dec. 1, 2010.

(30) Foreign Application Priority Data

Dec. 1, 2010 (EP) .................................. 10015172

(51) Int. Cl.
*A61B 17/70* (2006.01)
*A61B 17/80* (2006.01)
*A61B 17/86* (2006.01)

(52) U.S. Cl.
CPC ....... *A61B 17/7037* (2013.01); *A61B 17/8047* (2013.01); *A61B 17/863* (2013.01); *A61B 17/8605* (2013.01); *A61B 17/809* (2013.01)

(58) Field of Classification Search
CPC .......... A61B 17/7032; A61B 17/7034; A61B 17/7035; A61B 17/7037; A61B 17/7038; A61B 17/7046; A61B 17/7059; A61B 17/7058; A61B 17/80; A61B 17/8033; A61B 17/8047; A61B 17/8052; A61B 17/8057; A61B 17/8695; A61B 17/863; A61B 17/8685; A61B 17/8042

USPC ........... 606/53, 60, 246–279, 300–320, 328, 606/280, 289–296

See application file for complete search history.

(56) References Cited

U.S. PATENT DOCUMENTS 3,741,205 A * 6/1973 Markolf et al. ............... 606/291
4,388,921 A * 6/1983 Sutter et al. .................... 606/71
(Continued)

FOREIGN PATENT DOCUMENTS

EP     0897697 A1     2/1999
FR     2903880 A1     1/2008

OTHER PUBLICATIONS

European Search Report dated Aug. 4, 2011 in related EP Application No. 10015172.9 in German, 15 pages.
(Continued)

*Primary Examiner* — Lynnsy Summitt
(74) *Attorney, Agent, or Firm* — Morrison & Foerster LLP (57) ABSTRACT

A fixation apparatus comprises a holder and a tension sleeve receiving a bone screw, wherein the bone screw has a shaft with a front thread and a head at the rear end, and the holder has a through borehole with a receiving seat, in which the tension sleeve is mounted and able to swivel, while the shaft has a thickening in a rear region, to the front of the head, whose width increases toward the head, and the width of the tension sleeve is larger than the width of the shaft immediately before the thickening and smaller than the greatest width of the thickening. When screwed in, the thickening widens the tension sleeve so that it is pressed by its envelope against the wall of the receiving seat. In this way, an angle-stable pressing is achieved for any given orientation of the bone screw.

42 Claims, 6 Drawing Sheets

(56) References Cited

U.S. PATENT DOCUMENTS

| | | | |
|---|---|---|---|
| 4,484,570 A * | 11/1984 | Sutter et al. | 606/282 |
| 5,047,029 A * | 9/1991 | Aebi et al. | 606/264 |
| 5,053,036 A * | 10/1991 | Perren et al. | 606/291 |
| 5,127,914 A * | 7/1992 | Calderale et al. | 606/65 |
| 5,151,103 A * | 9/1992 | Tepic et al. | 606/291 |
| 5,167,664 A * | 12/1992 | Hodorek | 606/306 |
| 5,501,684 A * | 3/1996 | Schlapfer et al. | 606/301 |
| 5,578,034 A * | 11/1996 | Estes | 606/281 |
| 5,607,428 A * | 3/1997 | Lin | 606/287 |
| 5,643,265 A * | 7/1997 | Errico et al. | 606/70 |
| 5,647,873 A * | 7/1997 | Errico et al. | 606/264 |
| 5,672,176 A * | 9/1997 | Biedermann et al. | 606/271 |
| 5,735,853 A * | 4/1998 | Olerud | 606/71 |
| 5,879,350 A * | 3/1999 | Sherman et al. | 606/270 |
| 5,882,350 A * | 3/1999 | Ralph et al. | 606/278 |
| 5,891,145 A * | 4/1999 | Morrison et al. | 606/266 |
| 5,899,904 A * | 5/1999 | Errico et al. | 606/256 |
| 5,902,303 A * | 5/1999 | Eckhof et al. | 606/60 |
| 5,904,683 A * | 5/1999 | Pohndorf et al. | 606/287 |
| 5,954,722 A * | 9/1999 | Bono | A61B 17/7059 606/281 |
| 5,976,141 A * | 11/1999 | Haag et al. | 606/292 |
| 6,010,503 A * | 1/2000 | Richelsoph et al. | 606/278 |
| 6,030,389 A * | 2/2000 | Wagner et al. | 606/71 |
| 6,039,740 A * | 3/2000 | Olerud | 606/309 |
| 6,053,917 A * | 4/2000 | Sherman et al. | 606/270 |
| 6,063,090 A * | 5/2000 | Schlapfer | 606/270 |
| 6,074,391 A * | 6/2000 | Metz-Stavenhagen et al. | 606/278 |
| 6,146,383 A * | 11/2000 | Studer et al. | 606/308 |
| 6,187,005 B1 * | 2/2001 | Brace et al. | 606/264 |
| 6,235,033 B1 * | 5/2001 | Brace et al. | 606/288 |
| 6,241,731 B1 * | 6/2001 | Fiz | 606/65 |
| 6,248,105 B1 * | 6/2001 | Schlapfer et al. | 606/266 |
| 6,306,136 B1 * | 10/2001 | Baccelli | 606/279 |
| 6,331,179 B1 * | 12/2001 | Freid et al. | 606/279 |
| 6,454,769 B2 * | 9/2002 | Wagner et al. | 606/279 |
| 6,471,705 B1 * | 10/2002 | Biedermann et al. | 606/271 |
| 6,575,975 B2 * | 6/2003 | Brace et al. | 606/86 B |
| 6,679,883 B2 * | 1/2004 | Hawkes et al. | 606/279 |
| 6,716,214 B1 * | 4/2004 | Jackson | 606/266 |
| 6,749,613 B1 * | 6/2004 | Conchy et al. | 606/57 |
| 6,835,196 B2 * | 12/2004 | Biedermann et al. | 606/308 |
| 6,890,334 B2 * | 5/2005 | Brace et al. | 606/281 |
| 6,902,567 B2 * | 6/2005 | Del Medico | 606/71 |
| 6,918,911 B2 * | 7/2005 | Biedermann et al. | 606/267 |
| 6,945,972 B2 * | 9/2005 | Frigg et al. | 606/256 |
| 7,001,389 B1 * | 2/2006 | Navarro et al. | 606/71 |
| 7,052,499 B2 * | 5/2006 | Steger et al. | 606/291 |
| 7,112,222 B2 * | 9/2006 | Fraser et al. | 623/17.11 |
| 7,135,021 B2 * | 11/2006 | Lin | 606/264 |
| 7,144,396 B2 * | 12/2006 | Shluzas | 606/266 |
| 7,175,623 B2 * | 2/2007 | Thramann et al. | 606/294 |
| 7,186,255 B2 * | 3/2007 | Baynham et al. | 606/266 |
| 7,195,633 B2 * | 3/2007 | Medoff et al. | 606/309 |
| 7,204,838 B2 * | 4/2007 | Jackson | 606/270 |
| 7,214,227 B2 * | 5/2007 | Colleran et al. | 606/273 |
| 7,276,070 B2 * | 10/2007 | Muckter | 606/71 |
| 7,303,564 B2 * | 12/2007 | Freid et al. | 606/86 B |
| 7,306,603 B2 * | 12/2007 | Boehm et al. | 606/279 |
| 7,306,606 B2 * | 12/2007 | Sasing | 606/279 |
| 7,316,715 B2 * | 1/2008 | Plaskon | 623/22.36 |
| 7,322,981 B2 * | 1/2008 | Jackson | 606/266 |
| 7,410,496 B2 * | 8/2008 | Derouet | 606/279 |
| 7,476,228 B2 * | 1/2009 | Abdou | 606/104 |
| 7,476,239 B2 * | 1/2009 | Jackson | 606/266 |
| 7,479,156 B2 * | 1/2009 | Lourdel et al. | 606/266 |
| 7,524,325 B2 * | 4/2009 | Khalili | 606/290 |
| 7,530,992 B2 * | 5/2009 | Biedermann et al. | 606/272 |
| 7,572,279 B2 * | 8/2009 | Jackson | 606/266 |
| 7,611,527 B2 * | 11/2009 | Freid et al. | 606/279 |
| 7,625,396 B2 * | 12/2009 | Jackson | 606/305 |
| 7,648,522 B2 * | 1/2010 | David | 606/266 |
| 7,651,516 B2 * | 1/2010 | Petit et al. | 606/279 |
| 7,662,175 B2 * | 2/2010 | Jackson | 606/300 |
| 7,682,379 B2 * | 3/2010 | Mathieu et al. | 606/289 |
| 7,686,837 B2 * | 3/2010 | Gasser et al. | 606/287 |
| 7,691,129 B2 * | 4/2010 | Felix | 606/246 |
| 7,722,652 B2 * | 5/2010 | Justis et al. | 606/267 |
| 7,731,736 B2 * | 6/2010 | Guenther et al. | 606/273 |
| 7,744,635 B2 * | 6/2010 | Sweeney et al. | 606/264 |
| 7,758,620 B2 * | 7/2010 | Porcher | 606/290 |
| 7,766,944 B2 * | 8/2010 | Metz-Stavenhagen | 606/266 |
| 7,766,947 B2 * | 8/2010 | Hawkes et al. | 606/280 |
| 7,771,458 B2 * | 8/2010 | Biedermann et al. | 606/289 |
| 7,776,067 B2 * | 8/2010 | Jackson | 606/246 |
| 7,789,900 B2 * | 9/2010 | Levy et al. | 606/300 |
| 7,794,482 B2 * | 9/2010 | Mathieu et al. | 606/290 |
| 7,833,250 B2 * | 11/2010 | Jackson | 606/270 |
| 7,833,251 B1 * | 11/2010 | Ahlgren et al. | 606/279 |
| 7,833,252 B2 * | 11/2010 | Justis et al. | 606/279 |
| 7,837,715 B2 * | 11/2010 | Petit et al. | 606/266 |
| 7,875,065 B2 * | 1/2011 | Jackson | 606/305 |
| 7,887,570 B2 * | 2/2011 | Ziolo et al. | 606/288 |
| 7,922,748 B2 * | 4/2011 | Hoffman | 606/267 |
| 7,931,678 B2 * | 4/2011 | Konieczynski et al. | 606/280 |
| 7,931,681 B2 * | 4/2011 | Carls et al. | 606/290 |
| 7,942,913 B2 * | 5/2011 | Ziolo et al. | 606/287 |
| 7,951,179 B2 * | 5/2011 | Matityahu | 606/300 |
| RE42,545 E * | 7/2011 | Ralph et al. | 606/266 |
| 7,981,142 B2 * | 7/2011 | Konieczynski et al. | 606/290 |
| 8,002,806 B2 * | 8/2011 | Justis | 606/264 |
| 8,007,523 B2 * | 8/2011 | Wagner et al. | 606/290 |
| 8,012,185 B2 * | 9/2011 | Warnick | 606/265 |
| 8,016,862 B2 * | 9/2011 | Felix et al. | 606/270 |
| 8,021,398 B2 * | 9/2011 | Sweeney et al. | 606/269 |
| 8,021,402 B2 * | 9/2011 | Martin et al. | 606/286 |
| 8,025,677 B2 * | 9/2011 | Freid et al. | 606/246 |
| 8,034,089 B2 * | 10/2011 | Matthis et al. | 606/306 |
| 8,048,131 B2 * | 11/2011 | Dalton | 606/305 |
| 8,052,724 B2 * | 11/2011 | Jackson | 606/265 |
| 8,066,751 B2 * | 11/2011 | Podgorski et al. | 606/290 |
| 8,075,600 B2 * | 12/2011 | Schlapfer | 606/266 |
| 8,075,602 B2 * | 12/2011 | Lombardo et al. | 606/290 |
| 8,075,603 B2 * | 12/2011 | Hammill et al. | 606/308 |
| 8,080,036 B2 * | 12/2011 | Shim et al. | 606/246 |
| 8,083,776 B2 * | 12/2011 | Alvarez | 606/265 |
| 8,092,504 B2 * | 1/2012 | Warnick | 606/269 |
| 8,100,946 B2 * | 1/2012 | Strausbaugh et al. | 606/266 |
| 8,114,140 B2 * | 2/2012 | Derouet | 606/305 |
| 8,118,849 B2 * | 2/2012 | Wahl et al. | 606/315 |
| 8,137,386 B2 * | 3/2012 | Jackson | 606/266 |
| 8,142,485 B2 * | 3/2012 | Buhren et al. | 606/289 |
| 8,172,885 B2 * | 5/2012 | Songer et al. | 606/290 |
| 8,182,517 B2 * | 5/2012 | Sixto et al. | 606/280 |
| 8,192,472 B2 * | 6/2012 | Sixto et al. | 606/280 |
| 8,197,517 B1 * | 6/2012 | Lab et al. | 606/268 |
| 8,211,154 B2 * | 7/2012 | Fisher et al. | 606/293 |
| 8,216,283 B2 * | 7/2012 | Mathieu et al. | 606/280 |
| 8,226,692 B2 * | 7/2012 | Mathieu et al. | 606/280 |
| 8,241,333 B2 * | 8/2012 | Jackson | 606/269 |
| 8,257,396 B2 * | 9/2012 | Jackson | 606/266 |
| 8,257,398 B2 * | 9/2012 | Jackson | 606/264 |
| 8,262,702 B2 * | 9/2012 | Giger et al. | 606/252 |
| 8,282,675 B2 * | 10/2012 | Maguire et al. | 606/289 |
| 8,287,575 B2 * | 10/2012 | Murner et al. | 606/287 |
| 8,303,633 B2 * | 11/2012 | Harris et al. | 606/286 |
| 8,361,126 B2 * | 1/2013 | Perrow et al. | 606/287 |
| 8,361,127 B2 * | 1/2013 | Biedermann et al. | 606/289 |
| 8,361,129 B2 * | 1/2013 | Chao | 606/305 |
| 8,377,102 B2 * | 2/2013 | Jackson | 606/269 |
| 8,388,665 B2 * | 3/2013 | Eberlein et al. | 606/290 |
| 8,388,666 B2 * | 3/2013 | Castaneda et al. | 606/290 |
| 2001/0021851 A1 * | 9/2001 | Eberlein et al. | 606/69 |
| 2002/0058939 A1 * | 5/2002 | Wagner et al. | 606/61 |
| 2004/0127896 A1 * | 7/2004 | Lombardo et al. | 606/61 |
| 2004/0143267 A1 * | 7/2004 | Fallin | 606/73 |
| 2004/0147928 A1 * | 7/2004 | Landry et al. | 606/61 |
| 2004/0254579 A1 * | 12/2004 | Buhren et al. | 606/71 |
| 2005/0055026 A1 * | 3/2005 | Biedermann et al. | 606/73 |
| 2005/0107796 A1 * | 5/2005 | Gerlach et al. | 606/69 |
| 2005/0154392 A1 | 7/2005 | Medoff et al. | |
| 2005/0171542 A1 * | 8/2005 | Biedermann et al. | 606/61 |
| 2005/0192580 A1 * | 9/2005 | Dalton | 606/73 |

(56) References Cited

U.S. PATENT DOCUMENTS

| | | | |
|---|---|---|---|
| 2005/0203516 A1* | 9/2005 | Biedermann et al. | 606/61 |
| 2006/0058797 A1* | 3/2006 | Mathieu et al. | 606/69 |
| 2006/0089644 A1 | 4/2006 | Felix | |
| 2006/0116678 A1* | 6/2006 | Impellizzeri | 606/69 |
| 2006/0149245 A1 | 7/2006 | Sweeney | |
| 2006/0235399 A1 | 10/2006 | Carls et al. | |
| 2007/0093818 A1* | 4/2007 | Biedermann et al. | 606/61 |
| 2007/0093826 A1* | 4/2007 | Hawkes et al. | 606/61 |
| 2007/0118126 A1* | 5/2007 | Medoff et al. | 606/69 |
| 2007/0225715 A1* | 9/2007 | Deffenbaugh et al. | 606/69 |
| 2007/0233116 A1* | 10/2007 | Olerud | A61B 17/8047 606/86 A |
| 2008/0119895 A1* | 5/2008 | Manceau | 606/280 |
| 2008/0132957 A1* | 6/2008 | Matthis et al. | 606/301 |
| 2008/0140130 A1* | 6/2008 | Chan et al. | 606/280 |
| 2008/0208257 A1* | 8/2008 | Matthys | 606/278 |
| 2008/0234750 A1* | 9/2008 | Woods et al. | 606/291 |
| 2008/0243192 A1* | 10/2008 | Jacene et al. | 606/290 |
| 2008/0306550 A1* | 12/2008 | Matityahu | 606/290 |
| 2009/0036933 A1* | 2/2009 | Dube et al. | 606/282 |
| 2009/0048634 A1* | 2/2009 | Jackson | 606/301 |
| 2009/0082819 A1* | 3/2009 | Blain et al. | 606/308 |
| 2009/0125069 A1* | 5/2009 | Sixto et al. | 606/286 |
| 2009/0192549 A1* | 7/2009 | Sanders et al. | 606/280 |
| 2009/0192550 A1* | 7/2009 | Leung et al. | 606/286 |
| 2009/0204155 A1* | 8/2009 | Aschmann | 606/264 |
| 2009/0210067 A1* | 8/2009 | Meridew | 623/22.24 |
| 2009/0222051 A1* | 9/2009 | Pengo | 606/305 |
| 2009/0248087 A1* | 10/2009 | Lewis et al. | 606/301 |
| 2009/0270927 A1* | 10/2009 | Perrow et al. | 606/286 |
| 2009/0287257 A1* | 11/2009 | Hagen | 606/289 |
| 2009/0287261 A1* | 11/2009 | Jackson | 606/305 |
| 2009/0326587 A1* | 12/2009 | Matthis et al. | 606/264 |
| 2010/0010540 A1* | 1/2010 | Park | 606/246 |
| 2010/0016904 A1* | 1/2010 | Jackson | 606/304 |
| 2010/0030280 A1* | 2/2010 | Jackson | 606/305 |
| 2010/0049255 A1* | 2/2010 | Matthis et al. | 606/279 |
| 2010/0057138 A1* | 3/2010 | Murner et al. | 606/308 |
| 2010/0069969 A1* | 3/2010 | Ampuero et al. | 606/301 |
| 2010/0094349 A1* | 4/2010 | Hammer et al. | 606/264 |
| 2010/0100137 A1* | 4/2010 | Justis et al. | |
| 2010/0114171 A1 | 5/2010 | Boachie-Adjei et al. | |
| 2010/0125302 A1 | 5/2010 | Hammill, Sr. et al. | |
| 2010/0179602 A1* | 7/2010 | Dauster et al. | 606/308 |
| 2010/0217334 A1* | 8/2010 | Hawkes | 606/305 |
| 2010/0234902 A1* | 9/2010 | Biedermann et al. | 606/305 |
| 2010/0249846 A1* | 9/2010 | Simonson | 606/264 |
| 2010/0262195 A1* | 10/2010 | Jackson | 606/305 |
| 2010/0318136 A1* | 12/2010 | Jackson et al. | 606/305 |
| 2010/0331887 A1* | 12/2010 | Jackson et al. | 606/264 |
| 2011/0009910 A1* | 1/2011 | Jackson | 606/305 |
| 2011/0015677 A1* | 1/2011 | Biedermann et al. | 606/264 |
| 2011/0015682 A1* | 1/2011 | Lewis et al. | 606/305 |
| 2011/0040338 A1* | 2/2011 | Jackson | 606/305 |
| 2011/0106176 A1* | 5/2011 | Jackson | 606/305 |
| 2011/0152945 A1* | 6/2011 | Matityahu | 606/290 |
| 2011/0172666 A1* | 7/2011 | Heilman | 606/60 |
| 2011/0213424 A1* | 9/2011 | Biedermann et al. | 606/305 |
| 2011/0224737 A1* | 9/2011 | Lewis et al. | 606/290 |
| 2011/0230969 A1* | 9/2011 | Biedermann et al. | 623/17.16 |
| 2011/0270320 A1* | 11/2011 | Oh et al. | 606/290 |
| 2011/0282394 A1* | 11/2011 | Wagner et al. | 606/290 |
| 2011/0282399 A1* | 11/2011 | Jackson | 606/305 |
| 2012/0016365 A1* | 1/2012 | Freid et al. | 606/70 |
| 2012/0046700 A1* | 2/2012 | Jackson et al. | 606/305 |
| 2012/0059426 A1* | 3/2012 | Jackson et al. | 606/300 |
| 2012/0089192 A1* | 4/2012 | Biedermann | 606/280 |
| 2012/0089194 A1* | 4/2012 | Strausbaugh et al. | 606/301 |
| 2012/0089196 A1* | 4/2012 | Jackson | 606/305 |
| 2012/0095514 A1* | 4/2012 | Lombardo et al. | 606/290 |
| 2012/0136396 A1* | 5/2012 | Baker et al. | 606/289 |
| 2012/0143262 A1* | 6/2012 | Jensen et al. | 606/304 |
| 2012/0143264 A1* | 6/2012 | Matthis et al. | 606/305 |
| 2012/0215264 A1* | 8/2012 | Lee | 606/305 |
| 2012/0259371 A1* | 10/2012 | Mathieu et al. | 606/289 |
| 2012/0265257 A1* | 10/2012 | Jackson | 606/304 |
| 2012/0303071 A1* | 11/2012 | Black et al. | 606/305 |
| 2012/0310284 A1* | 12/2012 | Gerchow | 606/264 |
| 2012/0310291 A1* | 12/2012 | Jackson | 606/305 |
| 2013/0018426 A1* | 1/2013 | Tsai et al. | 606/290 |

OTHER PUBLICATIONS

FR2903880 published Jan. 25, 2008, abstract only in English, downloaded from espacenet.com, 2 pages.

* cited by examiner

VARIABLE ANGLE BONE SCREW FIXATION ARRANGEMENT

CROSS REFERENCE TO RELATED APPLICATIONS

This application claims the benefit of U.S. Provisional Application No. 61/418,662, filed Dec. 1, 2010. This application also claims the priority of European Patent Application No. 10015172.9, filed Dec. 1, 2010.

FIELD OF THE INVENTION

The invention relates to a fixation apparatus for fastening by means of a bone screw. The fixation apparatus serves in particular for connection to a support rod for an implant, but it can also be used by itself.

BACKGROUND OF THE INVENTION

Screws are often used for a removable yet also sufficiently firm attachment of implants. Depending on the application, a rigid-angle positioning between the implant and the bone screw is sufficient; in other cases, however, a variable-angle (polyaxial) arrangement of the bone screws is required. Such a polyaxially mounted bone screw for a fixation apparatus is known in its basic features from EP 0 614 649 B1. The bone screw is led through a support sleeve, which has a screw-on nut for the securing. In order to attach the rod of an implant, a transverse borehole is provided in the support sleeve, through which the rod can be passed in an intermediate region between the nut and the bone screw. By tightening the nut, the rod is braced against the support sleeve. Large tightening forces can twist the support sleeve, which endangers the fastening safety.

In a further developed design, as is known from U.S. Pat. No. 7,641,674 B2, a pressure screw screwed into the rear end of the support sleeve acts on a tensioning element by a support rod of the implant that is inserted through a transverse bore, which has at its front end a dome-shaped recess to receive a spherically thickened screw head of the bone screw. The tensioning element can move lengthwise and is pressed by the force of the pressure screw against a snap ring arranged at the front end of the support sleeve. Thus, it forms an abutment for the pressing force applied by the pressure screw. This design limits the pressing forces which can be applied, and thus the clamping forces needed to achieve an angle stability.

SUMMARY OF THE INVENTION

A problem on which the invention is based is to create an improved fixation apparatus, starting from the above-mentioned prior art, that achieves a better angle fixation.

This can be achieved by a fixation apparatus with the features as broadly disclosed herein. Advantageous further developments are described in the detailed embodiments below.

In a fixation apparatus comprising a holder and a tension sleeve receiving a bone screw, wherein the bone screw has a shaft with a front thread and a head at the rear end, and the holder has a through borehole with a receiving seat, in which the tension sleeve is mounted and able to swivel, the invention specifies that the shaft has a thickening in its rear region, to the front of the head, whose width increases toward the head, and the width of the tension sleeve is larger than the width of the shaft immediately before the thickening and smaller than the greatest width of the thickening.

By "front" is meant the direction toward the tip and by "rear" is meant the direction toward the head of the bone screw.

The thickening increasing from front to rear reaches its greatest width on the head, which is larger than the clear width of the tension sleeve. Preferably, the thickening extends over a length that is at least two and a half times the length of the tension sleeve. It is especially preferable when the thickening is conical, namely, with a cone angle of at most 15 degrees, preferably at most 5 degrees.

By being able to swivel is meant here that the axis of the bone screw fixated by means of the tension sleeve can take up a freely adjustable angle to the axis of the through borehole in the holder. The adjustment range is preferably at least 15 degrees in each direction about the center axis of the through borehole.

The invention is based on the notion of using a combination of two features to substantially enhance the force securing the screw in its angle position. On the one hand, the arrangement of the thickening forward from the head of the bone screw prevents the bone screw from slipping out of the tension sleeve even under very high force loading. Thus, the bone screw can be tightened at the implant site, whereupon it is displaced axially forward. On the other hand, thanks to this axial movement, the thickening is moved into the tension sleeve and presses against its inner wall. In this way, the tension sleeve with its preferably spherical envelope surface is elastically widened and seizes the preferably complementary shaped, i.e., spherically domed, wall of the receiving seat. Depending on the type of thickening, one achieves a substantial force transmission in this way, over tenfold for a cone angle of 5 degrees. Thus, a pressure between tension sleeve and receiving seat can be effectively achieved. The bone screw is thereby fixed in the desired angle position by a press fitting.

Usually the thickening will have a smooth envelope surface. This allows for a friction-free tightening of the bone screw and a simplified axial movement relative to the tension sleeve. But it can also be provided to configure a secondary thread on the thickening. This preferably has the same lead as the thread on the shaft. It is especially preferable for the secondary thread to be a multiple thread. This simplifies the screwing in process, especially when the mating thread is but short. The mating thread can be formed in the tension sleeve, preferably on a shoulder running around the preferably cylinder-shaped inner wall of the tension sleeve. The shoulder prevents the bone screw from wandering out, and the inner thread arranged there facilitates the spreading of the tension sleeve and thus further increases the fastening safety.

In one preferred embodiment, the envelope of the thickening is provided with its own threading (secondary thread). The secondary thread is preferably configured with a lead that is smaller than the lead of the thread on the shaft, advisedly in the range of 0.4 to 0.6. Thus, the secondary thread is more fine than the thread on the shaft and therefore preferably a single-flight thread. But a multiple-flight design is not ruled out. In front of the envelope on which the secondary thread is formed there is preferably provided a conical segment by which the width increases from the width of the shaft to the width of the envelope. The envelope itself is advisedly cylindrical, but this is not compulsory. Preferably, the head is conical in design, so that it directly adjoins the thickening and broadens toward the rear.

It is not absolutely necessary for the thickening to rise up uniformly from the shaft. It can also be provided that the thickening forms a flange at its front end. It is especially expedient in this case to combine the thickening structurally with the head of the bone screw, and then the outer envelope of the thickening will have a conicity that can furthermore advantageously extend across to the head.

Moreover, it can be provided that the bone screw has a conical thread with a core diameter increasing toward the head. With such a thread, a good cutting action in the bone can be achieved with good fastening safety of simple implantation techniques.

The tension sleeve is preferably slotted. This can be accomplished in various ways. Thus, a slot can be provided running the entire length of the tension sleeve. This produces a good widening capacity, yet at the expense of a rotationally symmetrical transfer of force to the wall of the receiving seat. Alternatively (or also in addition), it can be provided to have several slots open at one end. Advisedly, they are open toward the front end.

The tension sleeve can be provided with a complex through opening. By this is meant that the through opening has a conical segment to accomplish the spreading function and a threaded segment that is preferably short (at most two turns of the screw) and serves for tensioning.

In an alternative embodiment providing special protection, the fixation apparatus comprises a screw and a holder, wherein the screw has a threaded shaft and a ball head, and the holder comprises a holding sleeve, a tensioning element and a pressing element, and the holding sleeve is a continuous inner borehole provided with a front snug fit for the tensioning element and a rear inner thread for the pressing element, and wherein the tensioning element is a tension cage, and in the installed state the ball head is enclosed beyond its region of greatest width and interacts with the snug fit via a conical boundary surface so that the tension cage is squeezed together in the forward direction under an axial displacement and is pressed against the ball head.

This is based on the notion of providing for a substantial boosting of the force securing the screw in its angle position by a combination of two features. This is achieved, on the one hand, in that the tension cage encircles the ball head of the screw around its equator, and thus the ball head is prevented from slipping or being forced out even under very high force loading. This is combined with the invention's specified conicity between the tension cage and its snug fit in the holding sleeve, whereby the pressing force applied by the pressing element causes a narrowing of the tension cage with the ball head of the screw accommodated inside. The envelope surface of the tension cage enclosing the ball head is pressed into the ball head with substantially enhanced force, thanks to the wedge effect, so that a pressing fit results. Thanks to this pressing fit, combined with the protection against slipping out even under very high force application, a very stable angle fixation is achieved.

In order to increase the pressing forces exerted by the tension cage, the tension cage is preferably provided with slots on its envelope surface that are open toward the front end. In this way, the tension cage even when substantially compressed can transmit the pressing forces generated by the conicity without hindrance to the ball head, and without any unwanted internal constraint being produced in the tension cage.

Advantageously, the pressing element acts on an outer edge of the end face of the tension cage. When the pressing force acts on the outer edge and not the center of the tension cage, there is a direct force transmission to the conical boundary surface between outer envelope surface of the tension cage and the snug fit. Moreover, this prevent the tension cage from being indented at the center under the load of the pressing force, which would create a force on the ball head pushing it out of the tension cage. This enhances the fastening safety.

Advantageously, the tension cage has a radially projecting edge at its forward end. This enables a preassembly of the tension cage in the holding sleeve so that the tension cage can be shoved from the front into the holding sleeve and—after passing the narrow point at the front edge of the holding sleeve—snap into its position, while the radially projecting edge is still situated outside of the narrow point and the tension sleeve is prevented from wandering backward toward the thread. The ball head of the bone screw can be pressed into this unit. With such a preassembly, the usefulness to the surgeon is substantially facilitated, and furthermore the high risk to the patient of a possible loss of parts is averted.

The conical boundary surface can be configured in any given way. It is preferable for the tension cage to have a conical outer edge. This can cooperate with a narrow point provided at the forward end of the inner borehole. Such a narrow point is easy to fabricate, since the remainder of the inner borehole can be essentially cylindrical in shape. However, it is not ruled out that the inner borehole tapers conically in the region of the snug fit as an alternative or additional feature.

In a preferred embodiment, the snug fit has two zones, wherein one segment is arranged on the sleeve and the other on the tension cage. The segment on the sleeve is the front segment, and immediately behind this the segment adjoins the tension cage. The rear segment on the tension cage has its greatest width at the transition to the front segment. The rear conical segment preferably adjoins smoothly, i.e., without a change in width. The tension cage according to this preferred embodiment is arranged in the rear segment and interacts with the segment formed as a hollow spherical shell such that the ball head, as described above, is enclosed beyond the equator. In the variant described here, the tension cage itself does not go beyond the equator. This two-part design is easy to assemble and ensures a good fastening of the ball head with little sensitivity to tolerances.

The tension cage has, at its rear end face, preferably a groovelike concavity formed to receive a support rod. More details on the support rod are discussed further below. The concavity ensures a form-fit with the support rod and, thus, an exact supporting of its position.

The tension cage is advisedly slotted laterally in its rear zone, and this preferably as a double slot. This creates spreadable tongues. They are advisedly dimensioned such that they engage with window like recesses at the inside of the sleeve. This affords an additional fixation of the tension cage along with the bone screw supported by it, preventing an unintentional loss of its positioning.

Preferably, the width of the inner bore in the rear thread region is greater than the width in the region of the snug fit. This enables an easy preassembly of the tension cage in the holding sleeve, namely, by introducing the tension cage from behind through the threaded segment into its position in the region of the snug fit. This allows the width of the front opening of the inner bore to be smaller than the width of the tension cage. In this way, the tension cage is protected against an unintentional wandering to the front.

Advisedly, the holding sleeve has a seat for a support rod of an implant. This allows one to achieve a secure fixation of the implant in the region of the bone in which the bone screw is inserted. Even complex implants can be fastened securely and stable in angle by this method. Advantageously, the seat is configured as a transverse borehole to the inner borehole of the holding sleeve, and this in the region of the transition between the rear inner thread and the front snug fit. In the installed condition, the rod is thus situated between the pressing element and the end face of the tension cage, on which the pressing element can act directly without the rod. When the rod is installed, the pressure is transmitted from the pressing element to the tension cage, i.e., indirectly, namely across the cross section of the rod. This accomplishes at the same time a fixation of the rod relative to the fixation apparatus with no further expense.

The transverse borehole preferably has a nonround cross section. In this way, a form-fitting connection can be achieved between rod and holding sleeve. This creates additional safety against unwanted twisting. The transverse bore does not necessarily have to have the same cross sectional shape as the rod, but rather advisedly the transverse bore is extended lengthwise in the direction of the longitudinal axis of the inner bore. This offers further adjustment room and ensures a secure fastening even when the tension cage is positioned quite far forward (to counterbalance a relatively thin ball head of the bone screw).

Preferably, the pressing element has a buttress thread, wherein the rearward pointing load flank is steeper than the other forward pointing flank. A load flank angle of 0° or a negative load flank angle has proved to work especially well.

In all embodiments the bone screw can be provided with a continuous borehole running along its central axis, i.e., it is cannulated. Thus, it can be inserted along a guide wire that is pushed through, accomplishing a very good positioning accuracy even under difficult access conditions.

BRIEF DESCRIPTION OF THE DRAWINGS

The invention will now be explained in reference to the enclosed drawing, which shows an advantageous sample embodiment. There are shown.

DETAILED DESCRIPTION OF THE INVENTION

Figure 1:
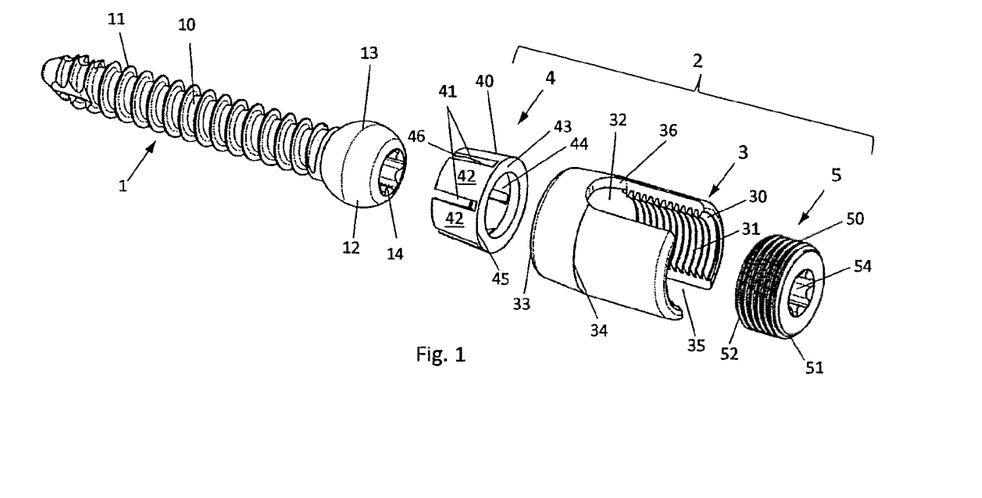
FIG. 1, an exploded view of the fixation apparatus according to a first embodiment of the invention.

The fixation apparatus comprises a holder 2 for a bone screw 1. The bone screw 1 is itself of conventional configuration with a shaft 10, on which a bone thread 11 is provided in its forward region or throughout. At the rear end of the shaft 10 is provided a screw head 12, which is spherically configured with an equator 13 at its largest diameter. At its rear end a star-shaped depression 14 can be provided as a seat for a correspondingly configured screwdriver.

Figure 3:
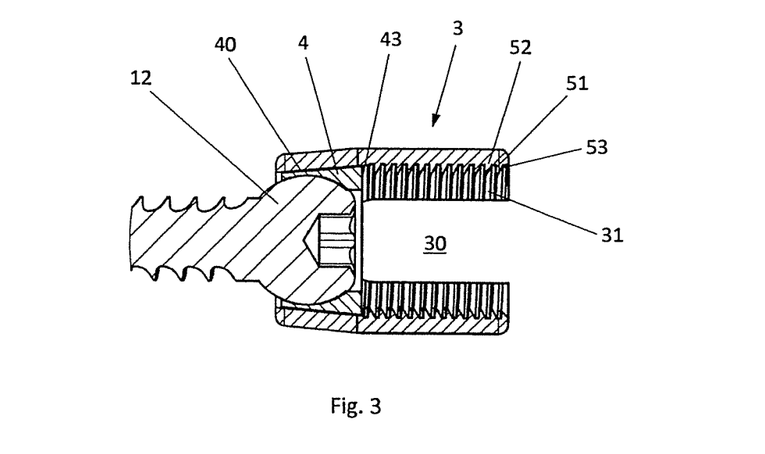
FIG. 3, a cross sectional view of the holding sleeve of the fixation apparatus.

The holder 2 comprises a sleeve 3, a tension cage 4 and a pressing element 5. The sleeve 3 has a hollow cylinder configuration with an inner opening 30 running from a rear to the front end. The inner opening 30 has an inner thread 31 in its rear area and a snug fit 32 provided with a smooth wall in its forward area. The core diameter of the inner thread 31 is chosen such that it is a bit smaller (around 1 mm) than the diameter in the region of the snug fit. The configuration of the wall in the region of the snug fit 32 is essentially cylindrical with a narrow point 33 at the forward end. Thus, a front mouth is formed with a decreased diameter.

The sleeve 2 furthermore has two diametrically opposite longitudinal slots 35. They extend from the rear end of the sleeve 3 across the entire region of the inner thread 31 as far as the transitional region 34 between inner thread 31 and snug fit 32. There, the slot 35 has a broadening in the tangential direction.

The tension cage 4 has an envelope surface 40 provided with a conical outer surface. this is divided by six slots 41 extending from the front end over around ⅘ of the length of the tension cage into a corresponding number of segments 42. These segments 42 are joined together by a holding ring 45, formed in the region of the rear end 43, and bordering a central installation opening 44. At the front ends of each of the segments 42 is formed an inwardly facing projection 46. The inner diameter of the tension cage 4 is chosen so that the ball head 12 of the screw 4 is accommodated therein with a slight play. The projection 46 protrudes so far inward that the segments 42 can only be moved under elastic spreading across the equator 13 of the ball head 12. This protects the ball head 12 of the screw 1 from an unintentional dropping out from the tension cage 4.

The pressing element 5 is configured as a headless screw with a buttress thread 51 on its outer envelope. At the rear end face, a star-shaped depression 54 is formed at the center to receive a screwdriver. The buttress thread 51 is configured such that the rearward pointing, load-bearing thread surface 52 is perpendicular to the envelope surface, while the other forward pointing thread surface 53 is inclined at an angle of around 70°. With this asymmetrical sawtooth configuration of the thread 51, a spreading of the holding sleeve 3 is prevented, even under heavy loading.

Figure 2:
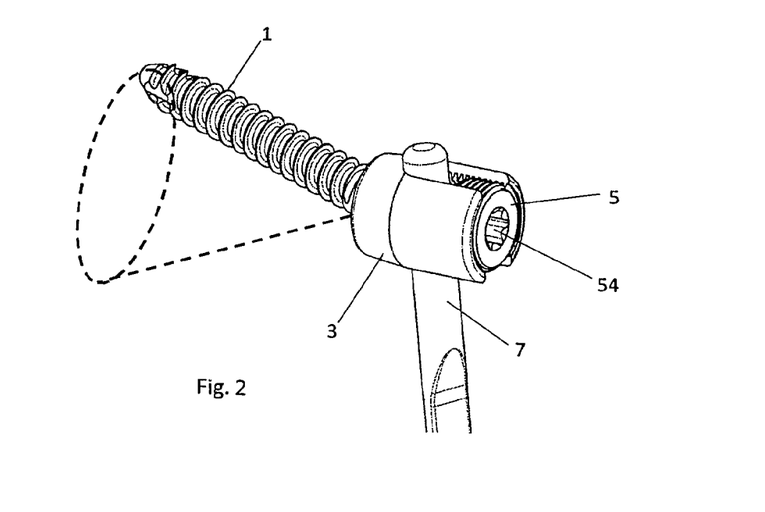
FIG. 2, an assembly view with rod of an implant installed.

For the assembly process, the cage 4 is guided from the front through the narrow point 33 under elastic compression of the segments 42, until the tension cage 4 comes to a stop in the region of the snug fit 32. In the installed state, the front ends of the segments 42 with the projection 46 stick out from the narrow point toward the front. In the next step, the screw 1 with its ball head 12 is inserted into the cage 4 under elastic spreading of the segments 42. Thus, these parts are captively preassembled. After this, the pressing element 5 can be installed by several turns in the inner thread 31. The forward part of the slot 35 with the widening 36 remains free. The fixation apparatus is now ready for use.

For the fastening of the implant, at first the bone screw 1 is tightened by a screwdriver led through the sleeve 3 to the star-shaped seat 14 in the ball head 12. In the next step, the rod 7 can be introduced into the transverse bore 35 for assembly. Finally, the pressing element 5 is screwed in and tightened by a screwdriver inserted into the depression 54. The pressure forces generated in this way are conveyed by the cross sectional rod 7 onto the end face 43 of the tension cage 4, so that the latter is moved forward in the axial direction. The resulting pressure forces are transformed by virtue of the conicity in the region of the boundary surface between outer envelope 40 of the tension cage 4 and the snug fit 32 in combination with the narrow point 33 into inwardly acting pressing forces that are higher by a multiple in magnitude and firmly press the ball-shaped screw head 12 together with the inside of the segments 42 of the tension cage 4. This achieves a stable-angle fixation.

The dotted line in FIG. 2 shows one possible region for the different angle that the polyaxial bearing of the screw 1 can take up in relation to the holder 3.

Figure 10:
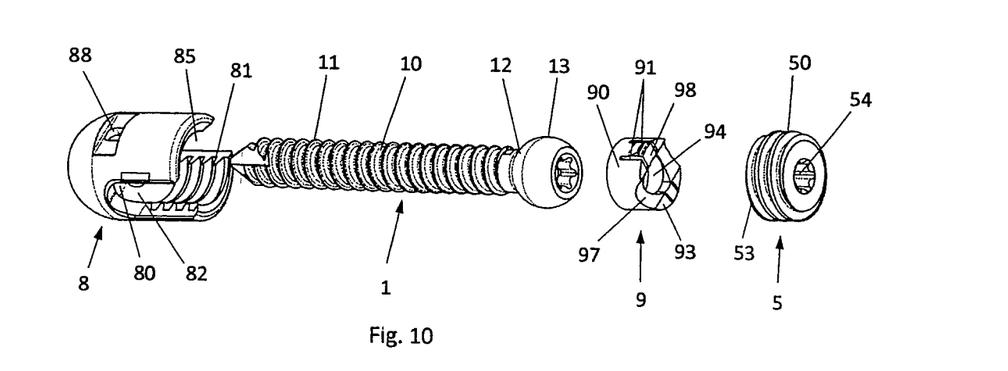
FIG. 10, an exploded view of the fixation arrangement according to a variant of the first embodiment.
Figure 11:
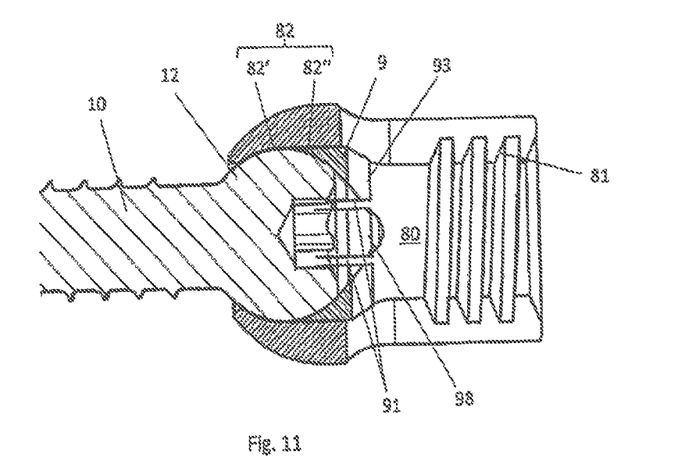
FIG. 11, a cross sectional view of the holding sleeve of the variant per FIG. 10.

One variant of the first embodiment is shown in FIGS. 10 and 11. Similar parts have the same reference numbers. The major difference lies in the configuration of the sleeve 8 and the tension cage 9. The sleeve 8 is a hollow cylinder with an inner bore 80 running through it from a rear end to the front end, being provided in its rear region with an internal thread 81 to accommodate the pressing element 5 and in its front region with a segment 82' of a snug fit 82 that is shaped as a hollow spherical segment. In the middle region there is provided an essentially smooth inner wall, against which the tension cage 9 bears with its envelope surface 90. The hollow spherical segment 82' of the snug fit 82 is shaped complementary to the ball head 12 of the bone screw 12. The opening at the front end of the sleeve 8 is narrowed and lets the shaft 10 pass through, but prevents the ball head 12 from going through.

The sleeve 8 furthermore has two diametrically opposite lengthwise slots 85. These extend from the rear end of the sleeve 8 across the entire region of the internal thread 81 and up to the snug fit 82. Two windowlike recesses 88 are arranged staggered from the lengthwise slots 85.

The tension cage 9 has an envelope 90 provided with a preferably conical outer surface, as well as an inner space 94. Its width is adapted to the width of the ball head 12 so as to produce a fit extending over one region. This region forms a second part 82" of the snug fit 82. It works together with the hollow spherical part 82' in such a way that a continuous snug fit 82 is formed to accommodate the ball head 12. The joining place between the two parts 82' and 82" lies in the region of greater width and thus where the equator 13 of the bone screw is situated.

In the rear zone of the tension cage are arranged pairs of slots 91 opposite each other, thus forming two diametrically opposite tongues 98. In the installed state of the tension cage 9, they spread out and fit into the windowlike recesses 88, thereby preventing the tension cage 9 from falling out from the sleeve 8. In this way, it is possible to form a preassembled unit from bone screw inserted in the sleeve 8 and tension cage 9. At its rear end face, the tension cage 9 is provided with a groove 97. This is preferably in the shape of a semicylinder and serves to receive a support rod of an implant 7 in form-fitting manner.

We shall now refer to the second embodiment. As can be seen from FIG. 4, the fixation apparatus comprises a holder 2' for a bone screw 1', having a shaft 10' with a bone thread 11' disposed in the forward region. Toward the rear end, the shaft 10' has an increasing thickness 15'. It extends as far as a head 12', which has a depression 14' to accommodate a screwdriver (not shown).

Figure 4:
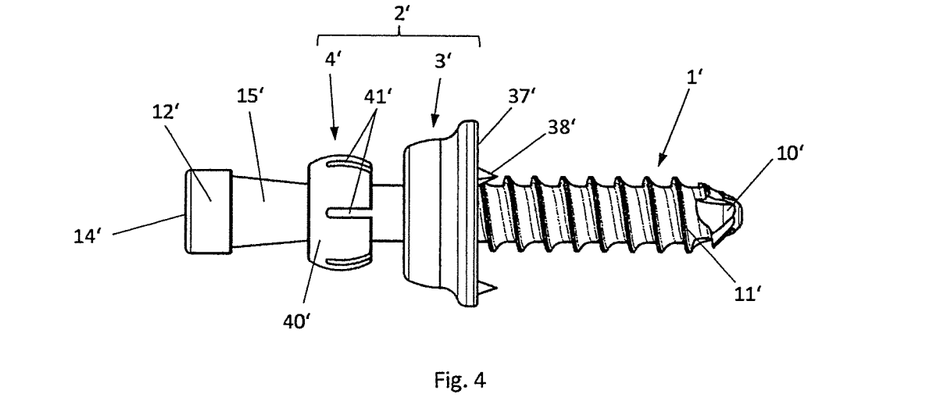
FIG. 4, a side view of a fixation apparatus according to a second embodiment of the invention.

The holder 2' comprises a base plate 3' and a tension sleeve 4'. The base plate 3' has a bearing surface 37' at its front end to bear against a bone or other tissue parts. It can be provided with optional support spikes 38'.

The base plate 3' has a support opening 30' passing through it, being widened to a snug fit 32' in the shape of a spherical dome in its middle region. This receives the tension sleeve 4', which in turn has a spherical envelope surface 40' with suitable dimensions. The tension sleeve 4' is mounted and able to swivel thanks to the complementary surfaces of the spherical envelope surface 40' on the one hand and the spherical dome-shaped snug fit 32' on the other. In this state, the fixation apparatus is preassembled and ready for implantation.

Figure 6A:
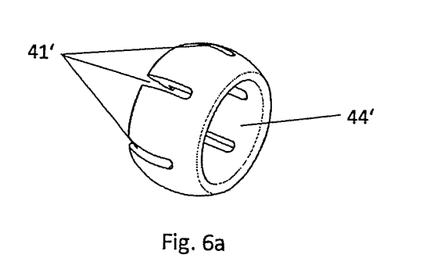
FIG. 6, perspective views of tension sleeves.
Figure 6B:
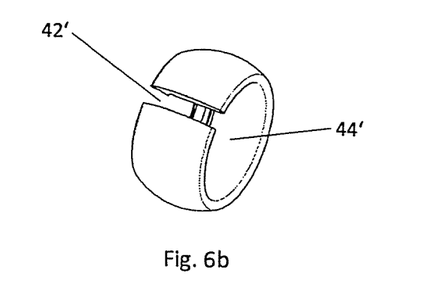
Figure 7A:
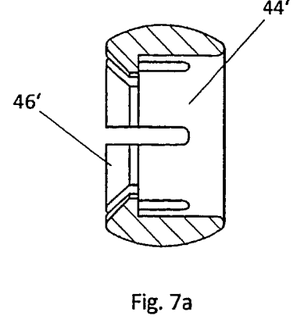
FIG. 7, sectional representations of tension sleeves.
Figure 7B:
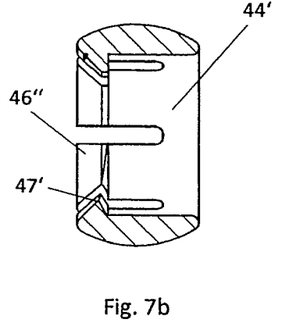

The tension sleeve 4' has a central opening 44', through which the bone screw 1' extends by its shaft 10' upon implantation. The opening 44' has an essentially cylindrical shape, with an inwardly pointing shoulder 46' at the front end (see FIG. 7a). Other sample embodiments for the opening 44', 44" are shown in FIG. 7b and c, namely, one with a complex shaped shoulder 46", on which one or two turns of an inner thread 47' are arranged, or a shoulderless design with opening narrowing conically to the front. Alternatively, however, the opening can also be cylindrical, if the shaft of the bone screw is conical in design. The tension sleeve 4' is preferably slotted, having several slots 41' open at one end (see FIG. 6a). But one continuous slot 42' can also be provided (see FIG. 6b).

Figure 5:
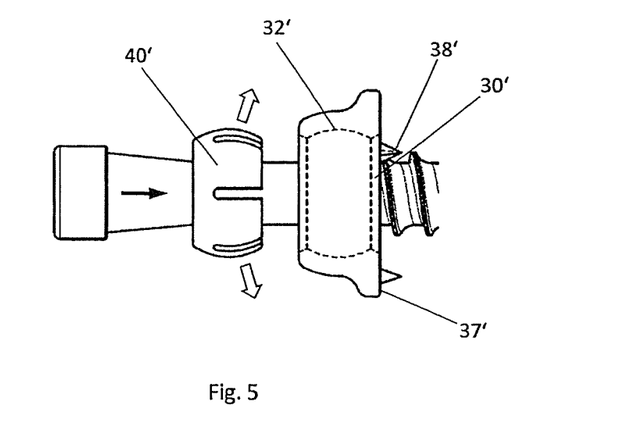
FIG. 5, a detail enlargement from FIG. 4.

The thickening 15' extends across a region that is around two to three times longer than the length of the tension sleeve 4' as dictated by the length of the opening 44'. When the screw 1' is twisted in, it moves axially forward by its shaft 10' through the base plate 3' (symbolized by the single arrow in FIG. 5). The conical thickening 15' comes into contact with the inner wall of the opening 44' and spreads open the tension sleeve upon further axial movement (see double arrow in FIG. 5). In this way, the tension sleeve 4' is forced by its spherical envelope surface 40' against the dome-shaped snug fit 32. This creates considerable forces on account of the small cone angle of less than 10 degrees, due to the wedge effect, so that this effectively produces a pressing together between tension sleeve 4' and snug fit 32' of the base plate 3'. The screw 1' is thus fixed in its particular swiveled angle position relative to the base plate 3'.

Figure 7C:
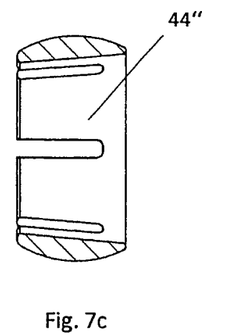
Figure 8A:
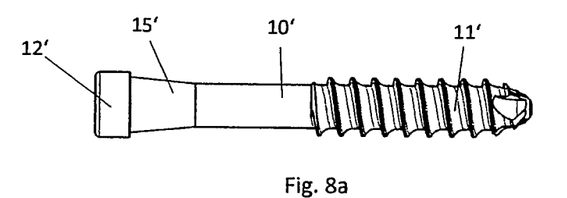
FIG. 8, various sample embodiments for thickenings of the bone screw.
Figure 8B:
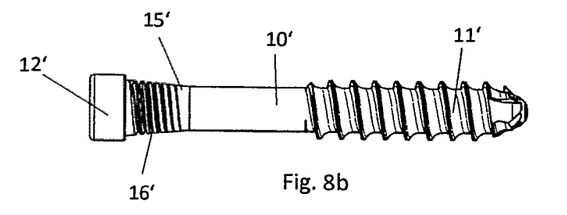
Figure 8C:
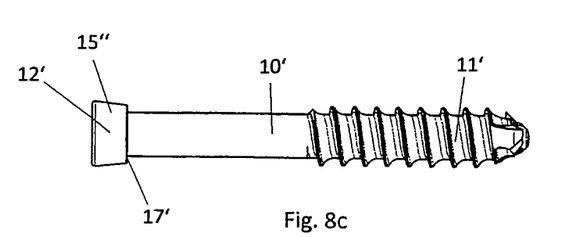

The thickening 15' can be conical, as described above. This is shown in FIG. 8a. Alternative embodiments are shown in FIG. 8b and c. Thus, the thickening 15' can be provided with a secondary thread 16'. This is a multiple thread, for easier insertion in the inner thread 47' on the tension sleeve 4' and it preferably has the same lead as the thread 11' on the shaft 10'. In this way, the axial force and thus the spreading and pressing action can be increased. Furthermore, the protection against unintentional loosening by backing off of the screw 1' in the bone is improved. In another alternative embodiment, the thickening 15" is moved further to the rear and has a forward pointing flange surface 17'. The conical region of the thickening can thus be shorter in design, so that a structural integration with the head 12' is made possible. This provides a bone screw 1' that is especially easy to fabricate. Preferably, the latter alternative will be used together with a type of tension sleeve 4' as depicted in FIG. 7c. This enables a unit of especially compact construction, thanks to its likewise conical opening 44", which is preferably complementary to the conicity of the thickening 15".

Figure 12:
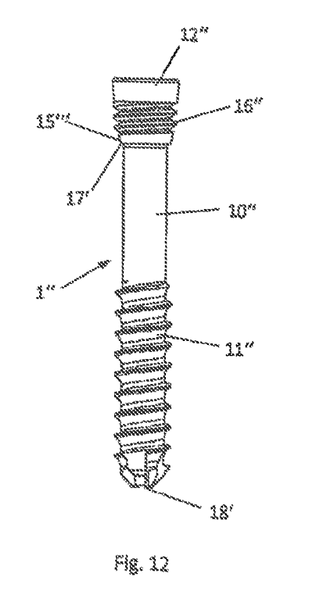
FIG. 12, a representation of a bone screw for a variant of the second embodiment.
Figure 13:
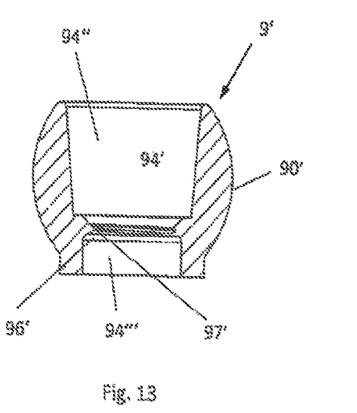
FIG. 13, a sectional view of a tension sleeve of the variant of the second embodiment.

One variant of the second embodiment is shown in FIGS. 12 and 13. Similar parts carry the same reference numbers. The bone screw 1" has a shaft 10" with a conical bone thread 11" arranged in the front region. At the rear end, the shaft 10" has a thickening 15''', adjacent to the head 12". The head 12" is designed to broaden conically to the rear, starting from the thickening 15'''. The thickening 15''' comprises a conical front segment in the region of the transition to the shaft 10"

and an envelope in the rear segment, on which a secondary thread 16" is formed. It has a lead that is somewhat less than half the lead of the bone thread 11" (for example, 7/15).

One variant of the tension sleeve 9' is shown in FIG. 13. It differs from the tension sleeves 4' shown in FIG. 7 basically by a complex configuration of the continuous opening 94'. This comprises a shorter front cylindrical part 94" and a longer rear conical part 94''', and at their transition is arranged an inwardly projecting radial strip 96' with a short internal thread 97'. By "short" is meant here up to two turns of the screw.

In this variant, the bone screw 1" widens by its thickening 15''' the cylindrical part 94''' of the complex continuous opening, and this under an advancing force that is produced by the secondary thread 16" engaging in the short internal thread 97' during the screwing in process. The conical shape of the head 12", together with the conical part 94''', ensures a further spreading and clamping of the bone screw 1", so that it is protected against unintentional loosening.

Figure 9:
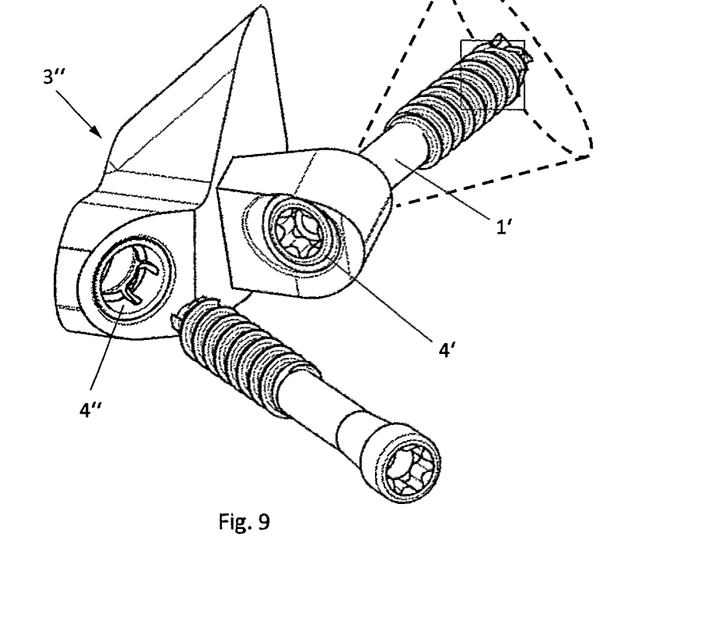
FIG. 9, a multiple holder for two bone screws.

The holder can also be configured so that several bone screws are supported. One example of this is shown in FIG. 9. This shows a multiple holder 3", having two receiving seats, in order to additionally accommodate a second tension sleeve 4".

The invention claimed is:

1. A fixation apparatus comprising:
a bone screw;
a holder; and
a tension sleeve configured to receive the bone screw,
wherein the bone screw comprises a shaft with a front thread, a thickened region with a secondary thread, and a head comprising a sidewall without a threaded region,
wherein the holder comprises a through borehole with a receiving seat, in which the tension sleeve is mounted and able to swivel, and
wherein the thickened region is forward of the head, and a width of the thickened region increases toward the head, wherein the secondary thread has a lead that is 0.4 to 0.6 times the lead of the front thread on the shaft and wherein a width of the tension sleeve is larger than a width of the shaft immediately before the thickened region and smaller than a width of the head.

2. The fixation apparatus of claim 1, wherein the thickened region has a cone angle of at most 15 degrees.

3. The fixation apparatus of claim 1, wherein the thickened region has a cone angle of at most 15 degrees and a greater length than a length of the tension sleeve.

4. The fixation apparatus of claim 1, wherein the thickened region has a conical front segment and an envelope surface on which the secondary thread is formed.

5. The fixation apparatus of claim 4, wherein the thickened region has a front flange.

6. The fixation apparatus of claim 1, wherein the thickened region is combined with the head.

7. The fixation apparatus of claim 1, wherein a boundary surface between the tension sleeve and the receiving seat is ball-shaped, an outer envelope of the tension sleeve being spherical.

8. The fixation apparatus of claim 1, wherein a cylindrical inner wall of the tension sleeve has an encircling, inwardly facing shoulder, the fixation apparatus further comprising an inner thread arranged on the inwardly facing shoulder.

9. A fixation apparatus of claim 1, wherein a width of the tension sleeve is larger than a width of the shaft immediately before the thickened region and smaller than a greatest width of the thickened region.

10. The fixation apparatus of claim 1, wherein the thickened region has a greater length than a length of the tension sleeve.

11. The fixation apparatus of claim 1, wherein the thickened region has a length that is at least two and a half times a length of the tension sleeve.

12. The fixation apparatus of claim 1, wherein the head broadens conically toward a rear end.

13. The fixation apparatus of claim 1, wherein the receiving seat is open to a rear end and forms a mouth, and wherein a width of the mouth is smaller than a width of a middle region of the receiving seat.

14. The fixation apparatus of claim 1, wherein the tension sleeve comprises a continuous opening comprising: a cylindrical segment and a conical segment and a transition between the cylindrical segment and the conical segment,
wherein a radial strip at the transition is arranged with a short internal thread.

15. A fixation apparatus comprising:
a bone screw;
a holder; and
a tension sleeve configured to receive the bone screw,
wherein the bone screw comprises a shaft with a front thread, a thickened region with a secondary thread, and a head comprising a sidewall without a threaded region,
wherein the holder comprises a through borehole with a receiving seat, in which the tension sleeve is mounted and able to swivel, and
wherein the thickened region is forward of the head, and a width of the thickened region increases toward the head, wherein the secondary thread has a smaller lead than the front thread on the shaft and wherein a width of the tension sleeve is larger than a width of the shaft immediately before the thickened region and smaller than a width of the head, and
wherein a cylindrical inner wall of the tension sleeve has an encircling, inwardly facing shoulder and an inner thread is arranged on the inwardly facing shoulder.

16. The fixation apparatus of claim 15, wherein the thickened region has a cone angle of at most 15 degrees.

17. The fixation apparatus of claim 15, wherein the lead of the secondary thread is 0.4 to 0.6 times the lead of the front thread on the shaft.

18. The fixation apparatus of claim 15, wherein a boundary surface between the tension sleeve and the receiving seat is ball-shaped, an outer envelope of the tension sleeve being spherical.

19. The fixation apparatus of claim 15, wherein the receiving seat is open to a rear end and forms a mouth.

20. The fixation apparatus of claim 15, wherein the tension sleeve is slotted.

21. The fixation apparatus of claim 20, further comprising a continuous slot running an entire length of the tension sleeve.

22. The fixation apparatus of claim 20, wherein the tension sleeve comprises a plurality of one-ended slots.

23. The fixation apparatus of claim 20, wherein the tension sleeve comprises a plurality of one-ended slots that are open toward a front end.

24. The fixation apparatus of claim 15, wherein the tension sleeve comprises a continuous opening comprising: a cylindrical segment and a conical segment.

25. The fixation apparatus of claim 15, wherein the holder is fashioned as a multiple holder with at least two receiving seats for tension sleeves.

26. The fixation apparatus of claim 15, wherein a width of the tension sleeve is larger than a width of the shaft immediately before the thickened region and smaller than a greatest width of the thickened region.

27. The fixation apparatus of claim 15, wherein the head broadens conically toward a rear end.

28. The fixation apparatus of claim 15, wherein the receiving seat is open to a rear end and forms a mouth, and wherein a width of the mouth is smaller than a width of a middle region of the receiving seat.

29. A fixation apparatus comprising:
a bone screw;
a holder; and
a tension sleeve configured to receive the bone screw,
wherein the bone screw comprises a shaft with a front thread, a thickened region with a secondary thread, and a head comprising a sidewall without a threaded region,
wherein the holder comprises a through borehole with a receiving seat, in which the tension sleeve is mounted and able to swivel, and
wherein the thickened region is forward of the head, and a width of the thickened region increases toward the head, wherein the secondary thread has a smaller lead than the front thread on the shaft and wherein a width of the tension sleeve is larger than a width of the shaft immediately before the thickened region and smaller than a width of the head, and
wherein the head broadens conically toward a rear end.

30. The fixation apparatus of claim 29, wherein the thickened region has a cone angle of at most 15 degrees.

31. The fixation apparatus of claim 29, wherein the thickened region has a cone angle of at most 15 degrees and a greater length than a length of the tension sleeve.

32. The fixation apparatus of claim 29, wherein the thickened region has a conical front segment and an envelope surface on which the secondary thread is formed.

33. The fixation apparatus of claim 32, wherein the thickened region has a front flange.

34. The fixation apparatus of claim 29, wherein the lead of the secondary thread is 0.4 to 0.6 times the lead of the front thread on the shaft.

35. The fixation apparatus of claim 29, wherein the thickened region is combined with the head.

36. The fixation apparatus of claim 29, wherein a boundary surface between the tension sleeve and the receiving seat is ball-shaped, in particular, an outer envelope of the tension sleeve being spherical.

37. The fixation apparatus of claim 29, wherein a cylindrical inner wall of the tension sleeve has an encircling, inwardly facing shoulder, the fixation apparatus further comprising an inner thread arranged on the inwardly facing shoulder.

38. The fixation apparatus of claim 29, wherein a width of the tension sleeve is larger than a width of the shaft immediately before the thickened region and smaller than a greatest width of the thickened region.

39. The fixation apparatus of claim 29, wherein the thickened region has a greater length than a length of the tension sleeve.

40. The fixation apparatus of claim 29, wherein the thickened region has a length that is at least two and a half times a length of the tension sleeve.

41. The fixation apparatus of claim 29, wherein the receiving seat is open to a rear end and forms a mouth, and wherein a width of the mouth is smaller than a width of a middle region of the receiving seat.

42. The fixation apparatus of claim 29, wherein the tension sleeve comprises a continuous opening comprising: a cylindrical segment and a conical segment and a transition between the cylindrical segment and the conical segment,
wherein a radial strip at the transition is arranged with a short internal thread.

\* \* \* \* \*